United States Patent [19]
Takeuchi et al.

[11] 4,200,376
[45] Apr. 29, 1980

[54] FLUORESCENT OPHTHALMOSCOPIC PHOTOGRAPHING APPARATUS

[75] Inventors: Masaya Takeuchi, Iwaki, Japan; Phillip H. Hendrickson, Basel, Switzerland

[73] Assignee: Tokyo Kogaku Kikai Kabushiki Kaisha, Japan

[21] Appl. No.: 927,799

[22] Filed: Jul. 25, 1978

[30] Foreign Application Priority Data

Jul. 25, 1977 [JP] Japan .................................. 52-89067

[51] Int. Cl.² ............................................. G03B 29/00
[52] U.S. Cl. .......................................... 354/62; 351/7
[58] Field of Search ............. 354/62; 351/7; 128/213, 128/215, 216, 218 P, 218 PA; 200/61.58 R

[56] References Cited
U.S. PATENT DOCUMENTS

| | | | |
|---|---|---|---|
| 3,914,032 | 10/1975 | Takano et al. .......................... | 354/62 |
| 4,068,932 | 1/1978 | Ohta et al. .............................. | 354/62 |
| 4,102,563 | 7/1978 | Matsumura et al. ................... | 354/62 |

OTHER PUBLICATIONS

"Fluorescein Fundus Photography," Ferrer, American Journal of Ophthalmology, Oct. 1965, pp. 587–591.

*Primary Examiner*—Russell E. Adams
*Attorney, Agent, or Firm*—Stevens, Davis, Miller & Mosher

[57] ABSTRACT

Fluorescent ophthalmoscopic photographing apparatus including an injector for a fluorescent agent and a photographing camera for taking a photograph of an eye fundus. A time counter is provided for indicating a count of time interval from the start of the injection to each instance when the photograph is taken. A switch is provided so as to be actuated when the injection is completed to thereby make a record of the time interval wherein the injection is performed.

4 Claims, 3 Drawing Figures

FLUORESCENT OPHTHALMOSCOPIC PHOTOGRAPHING APPARATUS

The present invention relates to fluorescent ophthalmoscopic photographing apparatus in which fluorescent photographs of eye fundus are taken after a fluorescent agent has been injected into the blood of a patient so as to investigate blood circulations in the eye fundus.

It has hithertofore been recognized as being effective in detecting several types of diseases to investigate blood circulation in the eye fundus. For this purpose, photographs of eye fundus are usually taken after injecting a fluorescent agent into the blood of patient. Conventional ophthalmoscopic photographing apparatus adopted for the purpose is so designed that the photographing camera is repeatedly actuated by an operator to take photographs at desired time intervals. The apparatus includes a timer device which is adapted to be started in response to a start of injection of the fluorescent agent for providing an indication of time so as to make it possible to investigate the relationship between the circulation of the agent and the time from the instance when the injection is started to the instance when the photograph is taken. However, since the images of the eye fundus thus photographed changes not only in accordance with the aforementioned time interval but also in accordance with the duration time of the injection, it has been impossible by the fluorescent eye fundus photographs taken in accordance with the conventional manner to have a satisfactory observation of blood circulation in an eye fundus.

It is therefore an object of the present invention to provide a fluorescent ophthalmoscopic photographing apparatus which has means for automatically recording the time from start to end of the injection of the fluorescent agent.

Another object of the present invention is to make it possible to record the time of injection of the fluorescent agent automatically through a minor modification of the fluorescent ophthalmoscopic photographing apparatus.

According to the present invention, the above and other objects can be accomplished by a fluorescent opthalmoscopic photographing apparatus including shutter and illumination control means for photographing, fluorescent agent injection means, first switch means adapted to be actuated in response to the start of the injection, second switch means adapted to be actuated in response to the end of the injection, time counting means, said first switch means being connected with timer control means so that a time count is started by the time counting means in response to the start of injection, said second switch means being connected with record control means so that the time count is recorded at the end of the injection. Means is provided for projecting information of the time count on the photographing film plane and the second switch means is preferably connected in such a manner that the actuation of the second switch means serves to operate the shutter and illumination control means so as to take a photograph with the record of the time count.

The above and other objects and features of the present invention will become apparent from the following descriptions of a preferred embodiment taking reference to the accompanying drawings, in which.

Figure 1:
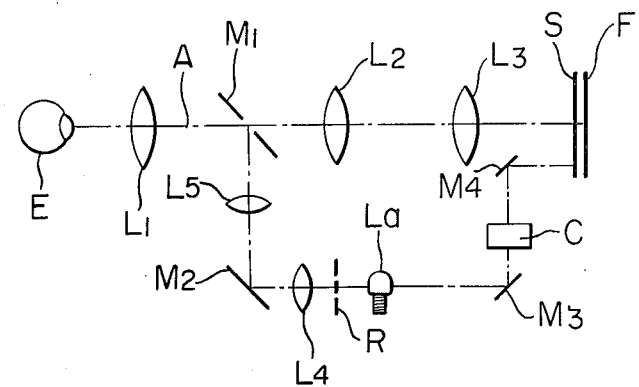
FIG. 1 is a diagrammatical view showing the optical system of an ophthalmoscopic photographing apparatus in which the present invention can be applied.

Referring to the drawings, particularly to FIG. 1, the optical system of an ophthalmoscopic photographing apparatus shown therein includes an objective lens $L_1$ adapted to be placed against a patient's eye E. Along the optical axis A of the objective lens $L_1$, there is disposed a relay lens $L_2$ and a focusing lens $L_3$ which projects the image of the fundus of the patient's eye E to a photographing film F. In front of the film F, there is disposed a shutter S which may be of a conventional design.

Between the lenses $L_1$ and $L_2$, there is disposed an apertured mirror $M_1$. The apparatus includes an illumination optical system which is comprised of an illumination lamp La, a ring-slit member R, a lens $L_4$, and a reflecting mirror $M_2$ for reflecting the light from the lamp La toward the mirror $M_1$ through a lens $L_5$. Thus, the illuminating light is directed through the objective lens $L_1$ to the eye E. A portion of the light from the lamp La is also passed toward a mirror $M_3$ to be reflected thereby and then passed through a time counter C to a mirror $M_4$ which functions to project the information in the counter C on the film F so that the time count in the counter C is recorded on the film F.

Figure 2:
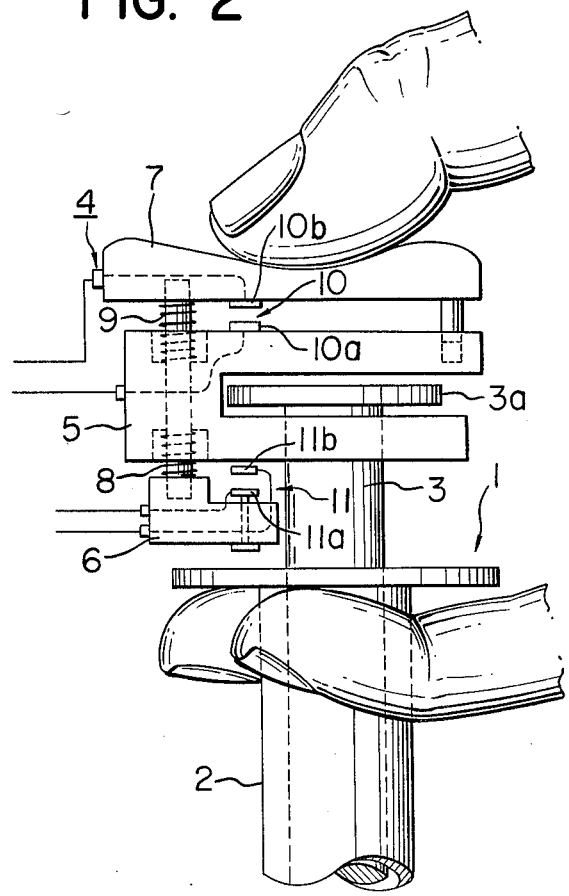
FIG. 2 is a fragmentary side view of a fluorescent agent injecting device embodying the feature of the present invention; and, FIG. 3 is a diagram showing a control circuit in accordance with one embodiment of the present invention.

Referring now to FIG. 2, there is shown an injector 1 comprised of a body or tube 2 and a plunger 3 slidably received in the body 2. The plunger 3 has a head 3 which carries a switch device 4. The switch device 4 comprises a stationary part 5 secured to the plunger head 3a, a movable part 6 disposed between the plunger head 3a and the injector body 2, and a movable part 7 disposed at the side of the plunger head 3a opposite to the movable part 6. The movable parts 6 and 7 are biased by means of springs 8 and 9, respectively, away from the stationary part 5.

The switch device 4 also has a first switch 10 including a stationary contact 10a on the stationary part 5 and a movable contact 10b on the movable part 7. The strength of the spring 9 is so determined that when the movable part 7 is forced toward the injector body 2 to start injection the part 7 is moved at first with respect to the stationary part 5 against the function of the spring 9 until the contacts 10a and 10b engage each other. The switch device 4 further comprises a second switch 11 including a contact 11a provided on the movable part 6 and a contact 11b provided on the stationary part 5. The spring 8 is so designed that it maintains the contacts 11a and 11b apart from each other during the injection and the contacts 11a and 11b are brought into engagement each other when the movable part 7 is further depressed after completion of injection.

Figure 3:
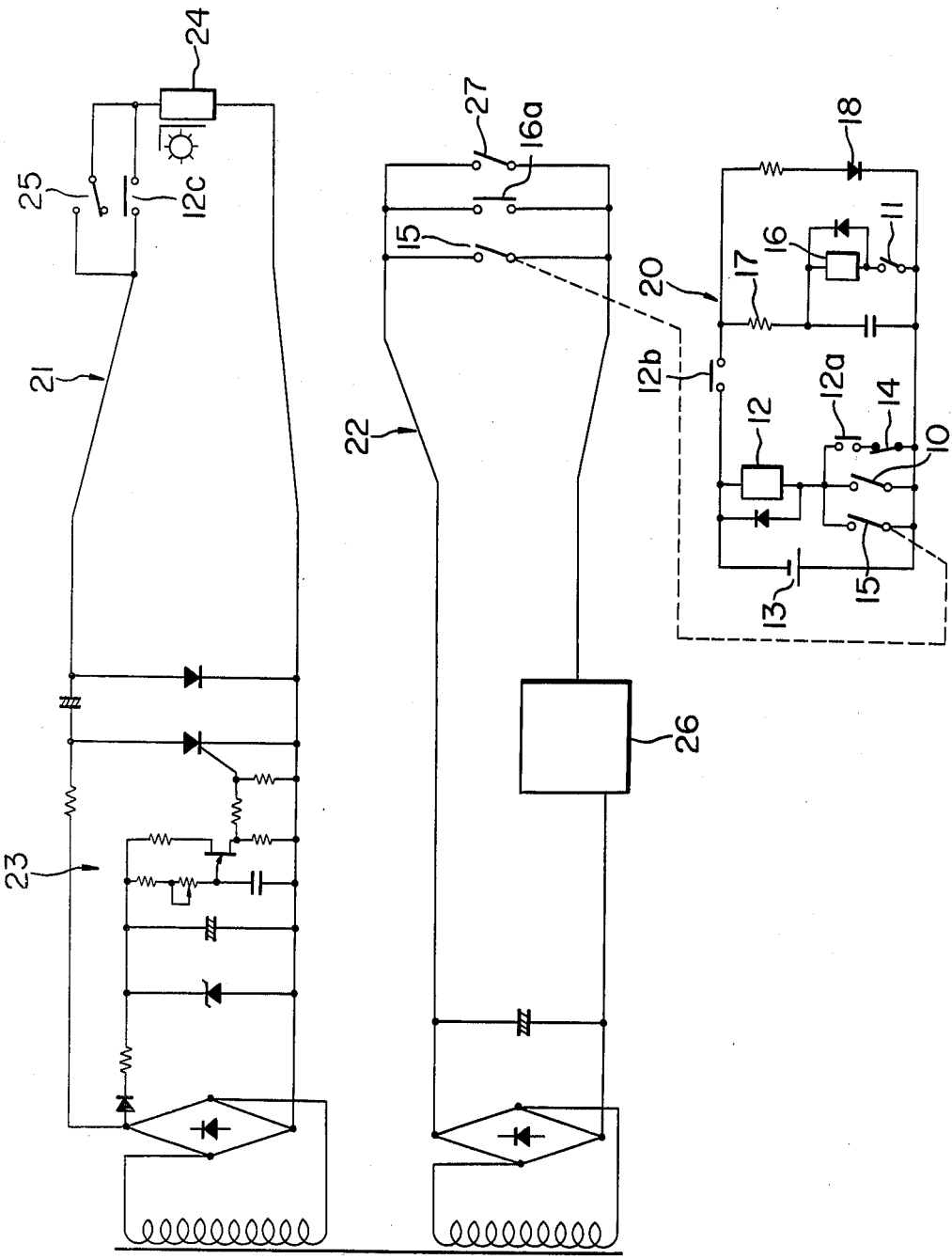

Referring to FIG. 3, there is shown a control circuit which comprises a control section 20 including the first and second switches 10 and 11, a time counting circuit 21 and a shutter and illumination control section 22. In the control section 20, the first switch 10 is connected in series with a solenoid 12 of a first relay and a DC power source 13. The first relay has a contact 12a which is connected with a reset switch 14. The contact 12a and the reset switch 14 are connected in parallel with the first switch 10 to constitute a self-holding circuit. A test switch 15 may be connected in parallel with the first switch 10.

The second switch 11 is connected in series with a solenoid 16 of a second relay which is in turn connected through a resistor 17 and a contact 12b of the first relay with a DC power source 13. The control section 20 further includes a light emitting diode 18 which is connected through the contact 12b with the power source 13.

The time counting circuit 21 comprises an oscillating circuit 23 and a counter 24, and a contact 12c of the first relay is between the oscillating circuit 23 and the counter 24. A manual switch 25 may be connected in parallel with the contact 12c. The shutter and illumination control section 22 includes a shutter and illumination circuit 26 which functions to control the operation of the shutter S and the illumination lamp La. Between the circuit 26 and the power source, there is a contact 16a of the second relay. In parallel with the contact 16a, there are connected a test switch 15a and a manual switch 27 for manual control of shutter release.

In the arrangement described above, when the injection of the fluorescent agent is started, the first switch 10 is closed and the solenoid 12 is therefore energized. The contact 12a is thus closed to establish the holding circuit. In this instance, the contact 12b is also closed so that the light emitting diode 18 is energized to provide an indication that the circuit is in operation. The contact 12c is simultaneously closed and the time counting circuit 21 is started to operate whereby a time count is made on the counter 24 to provide information regarding the time as measured from the start of injection.

When the injection has been completed, the second switch 11 is closed so that the solenoid 16 is momentarily energized. Thus, the relay contact 16a is closed to turn on the illumination lamp La and at the same time actuate the shutter S. Therefore, the information regarding the injection time count is projected on the film F to maintain the record of the injection time.

Thereafter, the manual switch 27 is repeatedly actuated to take photographs of eye fundus. In each photograph, a record of time as counted from the start of the injection is maintained because the value on the counter 24 is projected on the film F. After the photographing operations are completed, the reset switch 14 is actuated to break the holding circuit for the solenoid 12 to thereby terminate the operation of the time counting circuit 21. The counter 24 in the circuit 21 is reset to zero value by conventional means.

It will thus be understood that according to the present invention, the time counting device is started to operate at the time when the injection of the fluorescent agent is started and the time count on the device is automatically recorded at the end of the injection. It is therefore possible to perform an inspection of diseases more correctly by referring to the ophthalmoscopic photographs. The arrangement wherein a photograph is once taken automatically at the end of injection provides a further advantage from the viewpoint of economy because the concept of the present invention can be embodied by making minor modifications in a conventional fluorescent ophthalmoscopic photographing apparatus.

The present invention has thus been shown and described with reference to a specific embodiment, however, it should be noted that the invention is in no way limited to the details of the illustrated arrangements but changes and modifications may be made without departing from the scope of the appended claims.

We claim:

1. Fluorescent ophthalmoscopic photographing apparatus comprising photographing means for taking a photograph of eye fundus on a photographing film, shutter means for the photographing means, illumination means for illuminating a patient's eye, shutter and illumination control means for controlling actuation of the shutter and illumination means to take said photograph, fluorescent agent injection means, first switch means adapted to be actuated in response to the start of the injection, second switch means adapted to be actuated in response to the end of the injection, time counting means, means for projecting the time count onto the photographing film, said first switch means being connected with timer control means so that a time count is started by the time counting means in response to the start of the injection, record control means includes means for energizing said shutter and illumination control means to take a photograph of eye fundus together with a record of the time count, said second switch means being connected with said record control means so that the time count is recorded at the end of the injection.

2. Apparatus in accordance with claim 1 in which said injection means comprises a tubular injector body and a plunger slidably received in said body, said first and second switch means being mounted on said plunger.

3. Apparatus in accordance with claim 2 in which said first switch means comprises a pair of cooperating switch contacts, one being immovable with respect to the plunger and the other being mounted on a first member movable with respect to the plunger, spring means being provided between the plunger and the first member so as to bias the latter apart from the former, said spring means being of such strength that when the first member is depressed against the plunger for performing injection the spring means is compressed until the pair of contacts engage each other before the plunger starts to move.

4. Apparatus in accordance with claim 3 in which said second switch means comprises a pair of cooperating switch contacts, one being immovable with respect to the plunger and the other being mounted on a second member movable with respect to the plunger, said second member being located between the injector body and the plunger whereby said switch contacts of the second switch means being brought into engagement at final stage of injecting movement of the plunger.

* * * * *